(12) United States Patent
Sutradhar

(10) Patent No.: US 6,946,571 B2
(45) Date of Patent: Sep. 20, 2005

(54) DRYING OF ADIPIC ACID

(75) Inventor: Bhagya Chandra Sutradhar, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 109 days.

(21) Appl. No.: 10/674,308

(22) Filed: Sep. 30, 2003

(65) Prior Publication Data

US 2005/0070737 A1 Mar. 31, 2005

(51) Int. Cl.$^7$ .................. C07C 51/00; C07C 51/42; F26B 3/00
(52) U.S. Cl. .................. 562/590; 562/593; 34/496
(58) Field of Search .................. 562/590, 593; 34/496

(56) References Cited

U.S. PATENT DOCUMENTS 5,471,001 A * 11/1995 Anderson et al. ........... 562/593

* cited by examiner

Primary Examiner—Paul A. Zucker

(57) ABSTRACT

Process for drying moist, solid adipic acid using at least two drying stages in which moist solid adipic acid is progressively dried by contacting it in at least two successive stages with a nonreactive gas, the temperature of the first stage being lower than the temperature in any of the subsequent stages.

7 Claims, 1 Drawing Sheet

DRYING OF ADIPIC ACID

FIELD OF THE INVENTION

The invention relates to drying of moist adipic acid obtained after solid-liquid separation of a slurry from the crystallization of adipic acid from an aqueous solution thereof.

BACKGROUND OF THE INVENTION

Adipic acid is commercially produced by the oxidation of cyclohexanol and cyclohexanone by concentrated nitric acid. Initial product recovery and purification are accomplished through crystallization of the reaction mixture followed by solid-liquid separation. Additional purification of adipic acid is accomplished through one or more steps of aqueous recrystallization followed by solid-liquid separation. The solid cake from the solid-liquid separation unit after the final recrystallization step typically contains about 3 to 12 wt % water. This water is removed in a subsequent drying step in which heat is supplied to convert the water into vapor that is separated from solid adipic acid. A flow of gas is often used as the carrier of heat to be supplied to the moisture, as well as the carrier of the vapor to be removed. A typical desired moisture content of the dry adipic acid product is less than 0.2 wt %.

In the solid cake to be dried (as described above) the moisture is present in two forms: surface moisture (free moisture) and intrinsic (bound) moisture (including moisture present in liquid inclusions). Although the removal of free moisture is easy and fast, removal of bound moisture is difficult and slow. Therefore, practical drying processes usually use long residence time and high temperature in order to remove enough moisture so that the final product meets specification. However, at high temperature drying results in the formation of large amount of fine particles, presumably due to the dissolution of significant solid from particle surfaces by water prior to its vaporization. The dissolution should be more prominent if the moisture content of the moist adipic acid is high (e.g., 10 to 12%). Presence of so-called fines (very small particles) negatively impacts the loading-unloading characteristics of the product. It would therefore be desirable to have a drying process that would produce a product that meets moisture specification without forming excessive fine particles.

The present invention provides such a method of drying. In the present invention at least a portion of the water or more specifically at least a potion of the free moisture contained in moist adipic acid is removed by evaporation at low temperature prior to evaporating at high temperature the remaining water to be removed. Initial removal of water at low temperature should reduce dissolution and fines formation and drying at high temperature should remove the difficult to remove water contained in the solid.

SUMMARY OF THE INVENTION

The present invention is a method of removing at least a portion of water from moist, solid adipic acid that is obtained from solid-liquid separation of an adipic acid solution, the moist, solid adipic acid comprising adipic acid and water to produce a hot, dry adipic acid, said method comprising:

contacting the moist, solid adipic acid with a gas that does not react with adipic acid or water, in a succession of stages beginning with a first stage and terminating with a final stage, in which the moist, solid adipic acid is dried in the first stage by contacting the moist, solid adipic acid with the gas at a temperature in the range of 70 to 110 degrees C. to produce a partially-dried solid adipic acid, and, in at least one stage after the first stage, contacting the partially-dried solid adipic acid with the gas at a temperature in the range of 100 to 150 degrees C., the temperature in the first stage being lower than the temperature of any of said stages subsequent to said first stage.

DESCRIPTION OF DRAWING

The drawing consists of one figure.

DETAILED DESCRIPTION OF THE INVENTION

Figure 1:
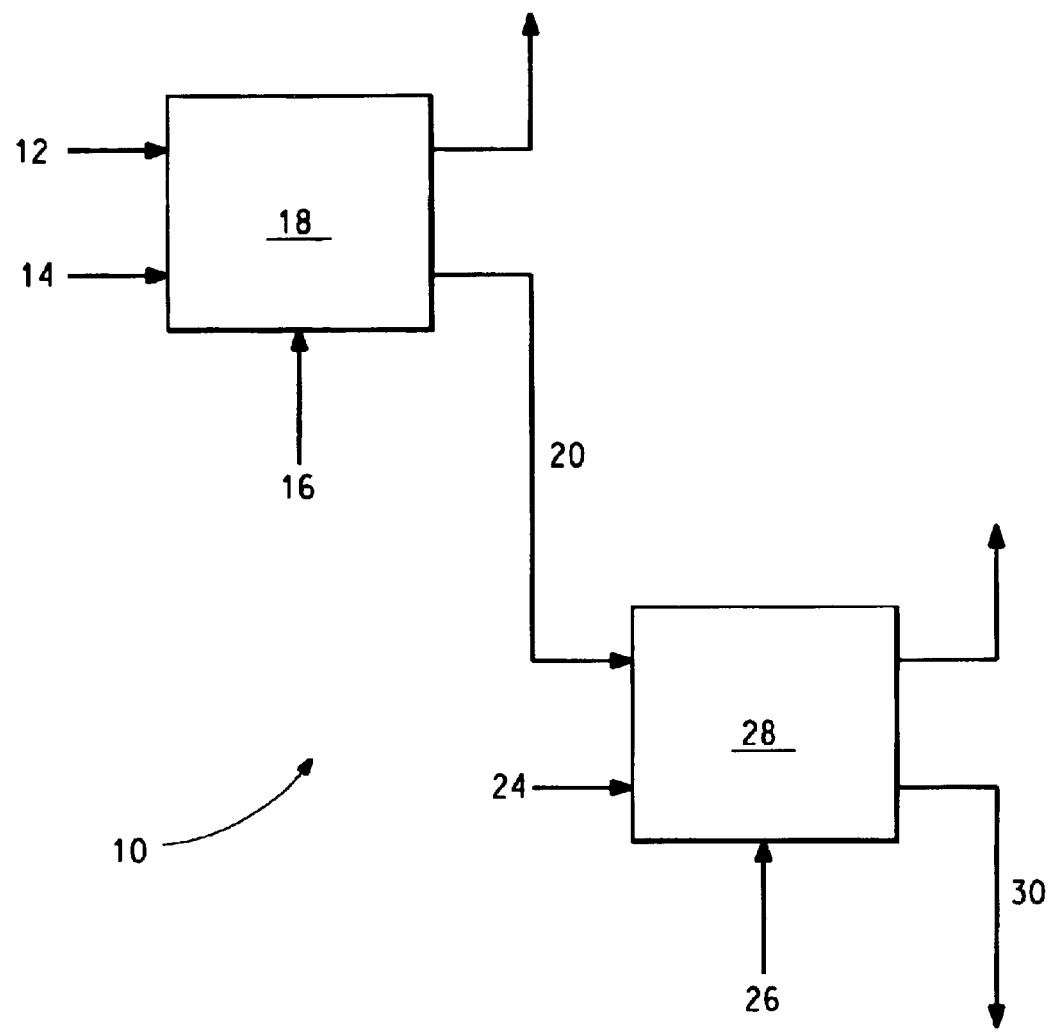
FIG. 1 depicts a block diagram of a process embodying the present invention.

Referring now to FIG. 1, there is shown a block diagram illustrating apparatus 10 that embodies one embodiment of the present invention involving only two stages in the drying process, namely, the first stage and the final stage.

Moist adipic acid containing more than 3 wt % water (12) and a drying gas (14) are fed to the first stage of drying (18). The drying gas (14) can be air, nitrogen or superheated steam or mixtures thereof. Other gases could be used, provided they do not react with either the adipic acid or the water. The drying gas (14) might be preheated. All or part of the required heat for drying (16) to the first stage can be provided through heat exchange surfaces. Radio-frequency (RF) or microwave energy also can be used to accomplish heating.

The first stage can be a vessel or part of a vessel in which the moist adipic acid is contacted with the drying gas in order to accomplish pre-drying. A rotary dryer (e.g. rotary drum dryer), a layer dryer (e.g. turbo tray dryer) or a fluidized bed dryer can be used as the first stage. The temperature of the gas in contact with the solid in the first stage can be within the range of 70 to 110 degrees C. and preferably in the range of 90 to 110 degrees C. The first stage can be a single unit or multiple units in series, and the temperature of the gas in contact with the solid can vary across the first stage. The total residence time (drying time) for first stage can be in the range of 5 to 120 minutes. A partially-dried, moist solid adipic acid after pre-drying (20) containing less than 3 wt % water, preferably containing less than 1 wt % water, is obtained from the first-stage.

The adipic acid after pre-drying (20) produced by the first stage and a drying gas (24) are fed to the final stage (28). The drying gas (24) can be air, nitrogen, superheated steam, or a mixture of at least two of these gases. The drying gas (24) can be preheated. All or part of the required heat for drying (26) to the final stage can be provided through heat exchange surfaces. Radio-frequency (RF) or microwave energy also can be used to accomplish heating.

The final stage of drying (28) is a vessel or part of a vessel in which partially-dried adipic acid is contacted with drying gas in order to produce a hot, dry adipic acid containing preferably less than 0.2 wt % water. A rotary dryer (e.g., rotary drum dryer), a layer dryer (e.g. turbo tray dryer) or a fluidized bed dryer can be used as the final stage. The temperature of the gas in contact with the solid in the final stage is within the range of 100 to 150 degrees C. The final stage might be a single unit or multiple units in series, and the temperature of the gas-solid mixture can vary across the final stage. The total residence time (drying time) of the final stage is in the range of 5 to 120 minutes.

The final stage produces a hot dry adipic acid (30). The first stage and the final stage and might be separate vessels or they might be separate compartments of one vessel. The temperature in the first stage (18) should be less than the temperature of any subsequent stages, including the final stage.

The first stage and the final stage can use the same type of dryer or different types of dryers. In one embodiment of the invention, a layer dryer might be used as the first stage, and a fluidized bed dryer might be used as the final stage.

A high flow rate of drying gas should be beneficial for both first stage and second stage. The flow rate, however, should be low enough so that excessive carry-over of solid adipic acid by drying gas is prevented.

In one embodiment of the invention, the hot, dry adipic acid produced by the final stage can be cooled down by contacting it with a cooling gas and maintaining a temperature in the range of 5 to 50 degrees C. for at least five minutes.

What is claimed is:

1. A method of removing at least a portion of water from moist, solid adipic acid that is obtained from solid-liquid separation of an adipic acid solution, the moist, solid adipic acid comprising adipic acid and water to produce a hot, dry adipic acid, said method comprising:

contacting the moist, solid adipic acid with a gas that does not react with adipic acid or water, in a succession of stages beginning with a first stage and terminating with a final stage, in which the moist, solid adipic acid is dried in the first stage by contacting the moist, solid adipic acid with the gas at a temperature in the range of 70 to 110 degrees C. to produce a partially-dried solid adipic acid, and, in at least one stage after the first stage, contacting the partially-dried solid adipic acid with the gas at a temperature in the range of 100 to 150 degrees C., the temperature in the first stage being lower than the temperature of any of said stages subsequent to said first stage.

2. The method of claim 1 further comprising cooling the hot, dry adipic acid contacting it with a gas that does not react with adipic acid or water, at a temperature in the range of 5 to 50 degrees C.

3. The method of claim 1 wherein the gas is selected independently for each of the stages from the group consisting of air, nitrogen, superheated steam and mixtures of at least two of the foregoing gases.

4. The method of claim 1 wherein heat is supplied through a heat exchange surface in one or more stages.

5. The method of claim 1 wherein the partially-dried solid adipic acid after contains less than 3 wt % water.

6. The method of claim 1 wherein the partially-dried solid adipic acid after contains less than 1 wt % water.

7. The method of claim 2 wherein the cooling gas is air or nitrogen.

* * * * *